United States Patent [19]

Alker et al.

[11] Patent Number: 5,397,800
[45] Date of Patent: Mar. 14, 1995

[54] CERTAIN 1-AZABICYCLO[2.2.1]HEPTANES USEFUL AS MUSCARINIC RECEPTOR ANTAGONISTS

[75] Inventors: David Alker, Birchington; Peter E. Cross; John E. G. Kemp, both of Canterbury, all of England

[73] Assignee: Pfizer Inc., New York, N.Y.

[21] Appl. No.: 861,876

[22] PCT Filed: Sep. 9, 1991

[86] PCT No.: PCT/EP91/01705
§ 371 Date: Feb. 25, 1993
§ 102(e) Date: Feb. 25, 1993

[87] PCT Pub. No.: WO92/05172
PCT Pub. Date: Apr. 2, 1992

[30] Foreign Application Priority Data

Sep. 13, 1990 [GB] United Kingdom ............... 9020051

[51] Int. Cl.[6] .................. C07D 487/02; C07D 487/08; A61K 31/40
[52] U.S. Cl. ..................................... 514/413; 548/453
[58] Field of Search ......................... 548/453; 514/413

[56] References Cited

U.S. PATENT DOCUMENTS

| | | | |
|---|---|---|---|
| 5,104,989 | 4/1992 | Cottrell et al. | 546/112 |
| 5,278,170 | 1/1994 | Orlek et al. | 514/304 |
| 5,314,899 | 5/1994 | Daly et al. | 514/339 |

Primary Examiner—Alan L. Rotman
Attorney, Agent, or Firm—Peter C. Richardson; Paul H. Ginsburg; Grover F. Fuller, Jr.

[57] ABSTRACT

MUSCARINIC RECEPTOR ANTAGONISTS OF THE FOLLOWING FORMULAE:

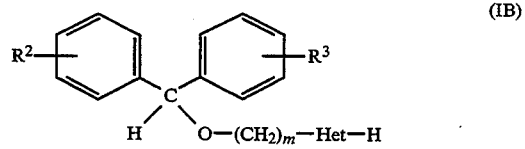

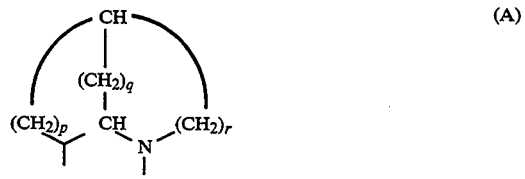

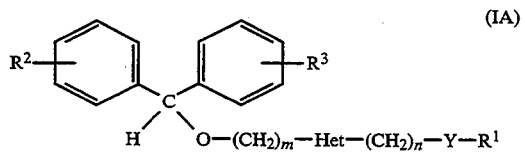

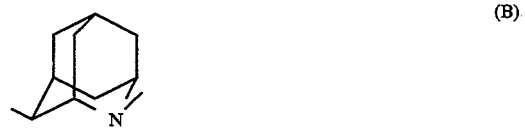

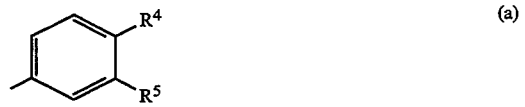

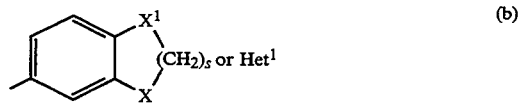

Muscarinic receptor antagonists, useful especially in the treatment of irritable bowel syndrome, of formula (IA) or (IB) or a pharmaceutically acceptable salt thereof, where $R^2$ and $R^3$ are each independently H, halo or $C_1$-$C_4$ alkyl; m is 0, 1 or 2; n is 1, 2 or 3; Y is a direct link, O or S; with the proviso that when n is 1, Y is a direct link; Het is a group of formula (A) or (B), where p is 0, (Abstract continued on next page.)

1 or 2, q is 1, 2 or 3, and r is 0, 1, 2 or 3, with the proviso that the sum of p, q and r is at least 3, the N atom of "Het" being attached to the group $(CH_2)_n$ in formula (IA) and to the H atom in formula (IB); and $R^1$ is a group of formula (a), (b) or $Het^1$, where $R^4$ and $R^5$ are each independently H, $C_1$–$C_4$ alkyl, $C_1$–$C_4$ alkoxy, —$(CH_2)_t$OH, halo, trifluoromethyl, cyano, —$(CH_2)_t$NR$^6$R$^7$, —CO($C_1$–$C_4$ alkyl), —OCO($C_1$–$C_4$ alkyl), CH(OH)($C_1$–$C_4$ alkyl), —C(OH)($C_1$–$C_4$ alkyl)$_2$, —SO$_2$NH$_2$, —$(CH_2)_t$CONR$^6$R$^7$ or —$(CH_2)_t$COO($C_1$–$C_4$ alkyl); $R^6$ and $R^7$ are each independently H or $C_1$–$C_4$ alkyl; t is 0, 1 or 2; X and $X^1$ are each independently O or $CH_2$; s is 1, 2 or 3; and $Het^1$ is pyridyl, pyrazinyl or thienyl.

6 Claims, No Drawings

CERTAIN 1-AZABICYCLO[2.2.1]HEPTANES USEFUL AS MUSCARINIC RECEPTOR ANTAGONISTS

This invention relates to certain azabicyclic compounds which are muscarinic receptor antagonists being selective for smooth muscle muscarinic sites over cardiac muscarinic sites. Thus the compounds are useful in the treatment of diseases associated with altered motility and/or tone of smooth muscle which can, for example, be found in the gut, trachea and bladder. Such diseases include irritable bowel syndrome, diverticular disease, urinary incontinence, oesophageal achalasia and chronic obstructive airways disease.

According to the invention there are provided compounds of the formula:

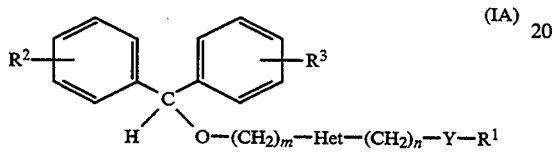

(IA)

and

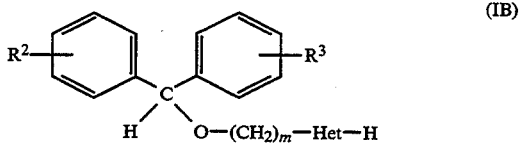

(IB)

and their pharmaceutically acceptable salts, where $R^2$ and $R^3$ are each independently H, halo or $C_1$-$C_4$ alkyl;

m is 0, 1 or 2;

n is 1, 2 or 3;

Y is a direct link, O or S; with the proviso that when n is 1, Y is a direct link;

Het is a group of the formula:

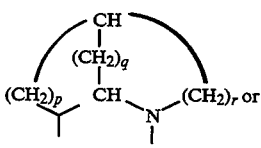 (A)

or

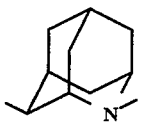 (B)

where p is 0, 1 or 2, q is 1, 2 or 3, and r is 0, 1, 2 or 3, with the proviso that the sum of p, q and r is at least 3, the N atom of "Het" being attached to the group $(CH_2)_n$ in formula (IA) and to the H atom in formula (IB); and $R^1$ is a group of the formula:

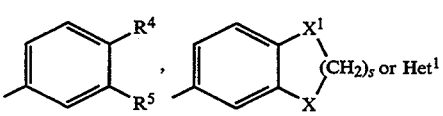

where $R^4$ and $R^5$ are each independently H, $C_1$-$C_4$ alkyl, $C_1$-$C_4$ alkoxy, —$(CH_2)_t$OH, halo, trifluoromethyl, cyano, —$(CH_2)_t NR^6R^7$, —$CO(C_1$-$C_4$ alkyl), —O-$CO(C_1$-$C_4$ alkyl), —$CH(OH)(C_1$-$C_4$ alkyl), —$C(OH)(C_1$-$C_4$ alkyl)$_2$ —$SO_2NH_2$, —$(CH_2)_t$-$CONR^6R^7$ or —$(CH_2)_t COO(C_1$-$C_4$ alkyl);

$R^6$ and $R^7$ are each independently H or $C_1$-$C_4$ alkyl;

t is 0, 1 or 2;

X and $X^1$ are each independently O or $CH_2$;

s is 1, 2 or 3; and $Het^1$ is pyridyl, pyrazinyl or thienyl.

"Halo" means F, Cl, Br or I. Alkyl and alkoxy groups of 3 or 4 carbon atoms can be straight or branched chain. The preferred alkyl and alkoxy groups are methyl, ethyl, methoxy and ethoxy.

$R^1$ is preferably a group of the formula:

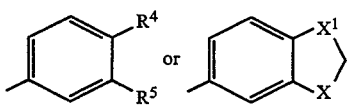

where $R^4$, $R^5$, X and $X^1$ are as defined above.

$R^1$ is more preferably:

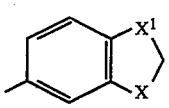

where X and $X^1$ are as defined above.

X and $X^1$ are both most preferably O.

$R^2$ and $R^3$ are both preferably H.

m is preferably 0 or 1.

n is preferably 1 or 2.

Y is preferably a direct link.

The sum of p, q and r is preferably 3 or 4.

In "Het", formula (A), preferably:

(i) p is 0, q is 2 and r is 1, (ii) p is 1, q is 1 and r is 1, (iii) p is 1, q is 2 and r is 1, or (iv) p is 2, q is 2 and r is 0.

It should be understood that the invention includes all the isomers of the compounds (IA) and (IB), e.g., where applicable, the syn and anti, and exo and endo forms, as well as racemates and separated enantiomers.

The pharmaceutically acceptable salts of the compounds of formula (I) include acid addition salts such as the hydrochloride, hydrobromide, sulphate or bisulphate, phosphate or hydrogen phosphate, acetate, besylate, citrate, fumarate, gluconate, lactate, maleate, mesylate, succinate and tartrate salts. For a more comprehensive list of pharmaceutically acceptable salts see, for example, the Journal of Pharmaceutical Sciences, Vol. 66, No. 1, January 1977, pages 1-19. These salts can be prepared conventionally, e.g. by mixing a solution of the free base and the acid in a suitable solvent, e.g. ethanol, and recovering the acid addition salt either as a precipitate, or by evaporation of the solution.

The compounds of the formula (IA) and (IB) can be prepared by a number of routes, including the following:

Route A

This route to the compounds (IA) can be illustrated as follows:

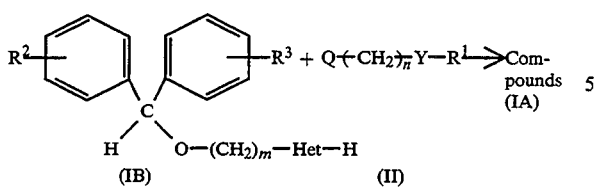

$R^1$, $R^2$, $R^3$, Y, Het, m and n are as defined for formula (IA) and Q is a leaving group, e.g. Br, Cl, I, $C_1$–$C_4$ alkanesulfonyloxy (e.g. methanesulfonyloxy), benzenesulfonyloxy, toluenesulfonyloxy (e.g. p-toluenesulfonyloxy) or trifluoromethanesulfonyloxy. Preferably, Q is Cl, Br, I or methanesulfonyloxy.

The reaction is preferably carried out in the presence of an acid acceptor such as sodium or potassium carbonate, triethylamine or pyridine, and in a suitable organic solvent, e.g. acetonitrile, at up to the reflux temperature. Reaction temperatures of 60°–120° C. are generally desirable and it is most convenient to carry out the reaction under reflux. Iodo is often a particularly suitable leaving group but since the starting materials (II) are sometimes most conveniently available as chlorides or bromides the reaction can also be carried out using the compound (II) as a chloride or bromide but in the presence of an iodide such as sodium or potassium iodide. In the preferred technique, the compounds (II) and (III) are refluxed together in acetonitrile in the presence of sodium carbonate and sodium iodide. The product (IA) can be isolated and purified conventionally.

The preparation of the compounds (IB) is described subsequently.

The starting materials of the formula (II) are in general known compounds which can be prepared by conventional techniques. The preparation of any novel starting materials of the formula (II) used in the Examples is however described in the following Preparations section.

Route B

This route to the compounds (IB) can be illustrated as follows:

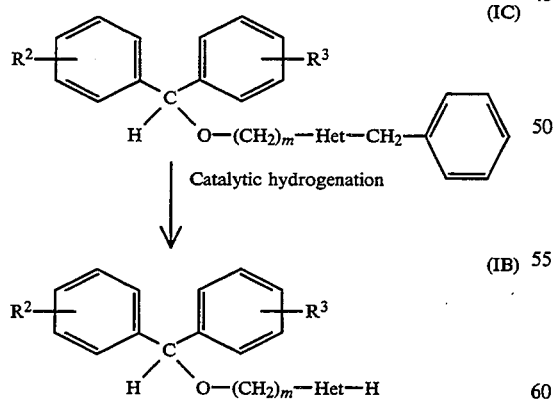

where $R^2$, $R^3$, Het and m are as defined for formula (IB)

The hydrogenation can be carried out conventionally, e.g. in ethanol at 40°–50° C. in the presence of palladium-on-charcoal and optionally acetic acid at a hydrogen pressure of about 50 psi (344.7 kPa).

The starting materials (IC) can be prepared as described in Route C.

Route C

This route to the compound (IC) can be illustrated as follows:

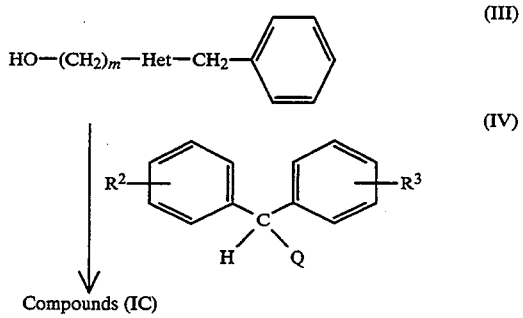

Q is either a leaving group as defined in Route A (preferably Br) or is a hydroxy group. When Q is a leaving group, the reaction is typically carried out by heating the reactants together at 140°–150° C. Sometimes the reaction is best carried out in an organic solvent such as xylene under reflux. When Q is OH, the reaction is typically carried out under reflux in an organic solvent such as toluene and in the presence of a dehydrating agent such as p-toluenesulphonic acid.

The compounds (III), if not commercially available, are either known compounds [see e.g. J. Org. Chem., 3822, 39 (1974); J. Org. Chem., 3091, 38 (1973); U.S. Pat. No. 4,013,668; J. Het. Chem., 395, 9 (1972] or are preparable by conventional techniques (see e.g. Preparations 1 to 4).

Route D

This route is useful for preparing compounds in which n is 2, Y is a direct link and $R^1$ is 2- or 4-pyridyl or pyrazinyl, and can be described as follows:

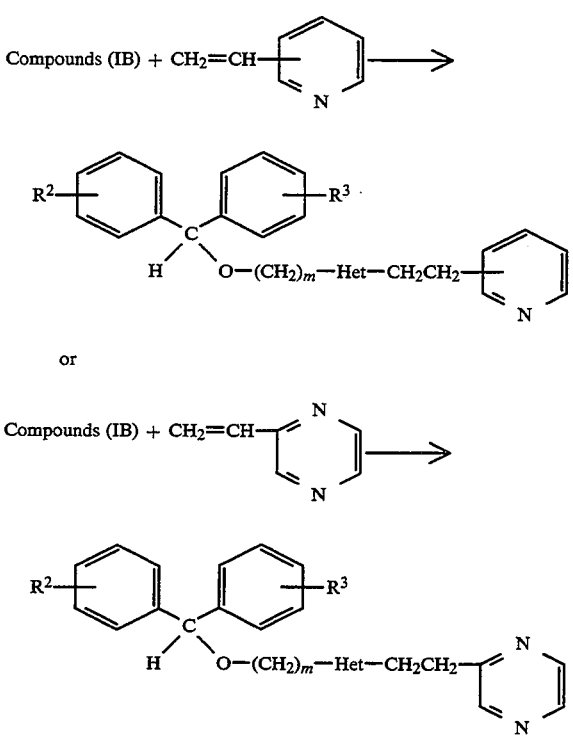

$R^2$, $R^3$, m and Het are as defined for formula (I). Clearly the vinyl group must be attached to the 2- or 4-position of the pyridine ring.

The reaction is typically carried out with heating, e.g. at about 60° to 110° C. and preferably under reflux, in a suitable organic solvent, e.g. dioxan. In some instances, the use of a basic (preferably a strong base which is soluble in an organic solvent such as N-benzyltrimethylammonium hydroxide ["Triton B"]) or acidic (preferably a $C_1$-$C_4$ alkanoic acid) catalyst may be beneficial.

Some of the compounds of the formula (I) in which $R^1$ is a substituted phenyl group can be converted to other compounds of the formula (I) as follows:

(a) A —$CO_2(C_1$-$C_4$ alkyl) substituent on the phenyl group can be selectively reduced to —$CH_2OH$. Lithium aluminium hydride is the most suitable reducing agent. The reaction is typically carried in a suitable organic solvent, e.g. ether, at between 0° and room temperature. It is generally most convenient to use the starting material in the form of its methyl ester.

(b) A hydroxy substituent on the phenyl group can be converted to —$OCO(C_1$-$C_4$ alkyl) by acylation using a $C_1$-$C_4$ alkanoyl chloride or bromide, or an alkanoic anhydride of the formula $(C_1$-$C_4$ alkyl.$CO)_2O$. The presence of an acid acceptor is preferable. The reaction is typically carried out at about room temperature in a suitable organic solvent, e.g. dioxan.

(c) A —$CO(C_1$-$C_4$ alkyl) substituent on the phenyl group can be reduced to a substituent of the formula —$CH(OH)(C_1$-$C_4$ alkyl). A suitable reducing agent is sodium borohydride. The reaction is typically carried out at between 0° and room temperature in a suitable organic solvent, e.g. methanol.

(d) A —$(CH_2)_rCOO(C_1$-$C_4$ alkyl) substituent, preferably where the alkyl group is methyl, can be converted to —$(CH_2)_rCONR^6R^7$ by reaction with ammonia or the appropriate amine $R^6R^7NH$. When $R^6$ and $R^7$ are both H, the use of aqueous (0.880) ammonia is generally most convenient, although the reaction can be carried out using ammonia in an organic solvent such as methanol or ethanol, or ammonia neat in a bomb. Although in some instances the reaction may proceed at a satisfactory rate at room temperature, heating at up to 120°, preferably 60° to 100° C., is generally necessary. For volatile amines, the reaction is best carried out in a bomb.

(e) A hydroxy substituent can be converted to $C_1$-$C_4$ alkoxy firstly by reaction with a base such as potassium carbonate, and secondly by reaction with a $C_1$-$C_4$ alkyl iodide or bromide. The reaction is typically carried out in a solvent such as dioxan or acetone, and preferably under reflux.

(f) A hydroxymethyl or hydroxyethyl substituent on the phenyl group can be converted to —$CH_2NR^6R^7$ or —$(CH_2)_2NR^6R^7$ firstly by reaction with thionyl chloride and secondly by reaction with ammonia or the appropriate amine $R^6R^7NH$. The reaction with thionyl chloride is typically carried out with heating, preferably under reflux, in a solvent such as methylene chloride. The reaction with ammonia or the amine is typically carried out at in a solvent such as ethanol, and heating, e.g. under reflux, may be necessary.

(g) A —$CO(C_1$-$C_4$ alkyl) substituent can be converted to —$C(OH)(C_1$-$C_4$ alkyl)$_2$ by reaction with a $C_1$-$C_4$ alkyllithium or $C_1$-$C_4$ alkylmagnesium bromide, chloride, or iodide (e.g. methyllithium, methylmagnesium bromide, methylmagnesium iodide or methylmagnesium chloride). The reaction is typically carried out in a solvent such as ether at a temperature of from 0° C. to room temperature. and (h) An iodo substituent can be converted to $C_1$-$C_4$ alkoxycarbonyl by reaction, typically at about room temperature, with carbon monoxide in a $C_1$-$C_4$ alkanol containing a base [e.g. potassium carbonate] and a palladium (II) catalyst [e.g. bis(triphenylphosphine)palladium (II) chloride].

The selectivity of the compounds as muscarinic receptor antagonists can be measured as follows.

Male guinea pigs are sacrificed and the ileum, trachea, bladder and right atrium are removed and suspended in physiological salt solution under a resting tension of 1 g at 32° C. aerated with 95% $O_2$ and 5% $CO_2$. Contractions of the ileum, bladder and trachea are recorded using an isotonic (ileum) or isometric transducer (bladder and trachea). The frequency of contraction of the spontaneously beating right atrium is derived from isometrically recorded contractions.

Dose-response curves to either acetylcholine (ileum) or carbachol (trachea, bladder and right atrium) are determined using a 1-5 minute contact time for each dose of agonist until the maximum response is achieved. The organ bath is drained and refilled with physiological salt solution containing the lowest dose of the test compound. The test compound is allowed to equilibrate with the tissue for 20 minutes and the agonist dose-response curve is repeated until the maximum response is obtained. The organ bath is drained and refilled with physiological salt solution containing the second concentration of test compound and the above procedure is repeated. Typically four concentrations of the test compound are evaluated on each tissue.

The concentration of the test compound which causes a doubling of the agonist concentration to produce the original response is determined ($pA_2$ value—Arunlakshana and Schild (1959), Brit. J. Pharmacol., 14, 48–58). Using the above analytical techniques, tissue selectivity for muscarinic receptor antagonists is determined.

Activity against agonist induced bronchoconstriction or gut or bladder contractility in comparison with changes in heart rate is determined in the anaesthetised dog. Oral activity is assessed in the conscious dog determining compound effects on, for example, heart rate, pupil diameter and gut motility.

Compound affinity for other cholinergic sites is assessed in the mouse after either intravenous or intraperitoneal administration. Thus, the dose which causes a doubling of pupil size is determined as well as the dose which inhibits the salivation and tremor responses to intravenous oxotremorine by 50%.

For administration to man in the curative or prophylactic treatment of diseases associated with the altered motility and/or tone of smooth muscle, such as irritable bowel syndrome, diverticular disease, urinary incontinence, oesophageal achalasia and chronic obstructive airways disease, oral dosages of the compounds will generally be in the range of from 3.5 to 350 mg daily for an average adult patient (70 kg). Thus for a typical adult patient, individual tablets or capsules will typically contain from 1 to 250 mg of active compound, in a suitable pharmaceutically acceptable vehicle or carrier for administration singly or in multiple doses, once or several times a day. Dosages for intravenous administration will typically be within the range 0.35 to 35 mg per single dose as required. In practice the physician will determine the actual dosage which will be most suitable for an individual patient and it will vary with the age, weight and response of the particular patient. The above dosages are exemplary of the average case but there can, of course, be individual instances where higher or lower dosage ranges are merited, and such are within the scope of this invention.

For human use, the compounds of the formula (IA) and (IB) can be administered alone, but will generally be administered in admixture with a pharmaceutical carrier selected with regard to the intended route of administration and standard pharmaceutical practice. For example, they may be administered orally in the form of tablets containing such excipients as starch or lactose, or in capsules or ovules either alone or in admixture with excipients, or in the form of elixirs or suspensions containing flavouring or colouring agents. They may be injected parenterally, for example, intravenously, intramuscularly or subcutaneously. For parenteral administration, they are best used in the form of a sterile aqueous solution which may contain other substances, for example, enough salts or glucose to make the solution isotonic with blood.

In a further aspect the invention provides a pharmaceutical composition comprising a compound of the formula (IA) or (IB), or a pharmaceutically acceptable salt thereof, together with a pharmaceutically acceptable diluent or carrier.

The invention also includes a compound of the formula (IA) or (IB) or a pharmaceutically acceptable salt thereof, for use as a medicament, particularly for use in the treatment of irritable bowel syndrome.

The invention further includes the use of a compound of the formula (IA) or (IB), or of a pharmaceutically acceptable salt thereof, for the manufacture of a medicament for the treatment of diseases associated with the altered motility and/or tone of smooth muscle, such as irritable bowel syndrome, diverticular disease, urinary incontinence, oesophageal achalasia and chronic obstructive airways disease.

The invention yet further includes a method of treatment of a human being to cure or prevent a disease associated with the altered motility and/or tone of smooth muscle, such as irritable bowel syndrome, which comprises treating said human being an effective amount of a compound of the formula (IA) and (IB), or a pharmaceutically acceptable salt or composition thereof.

The following Examples illustrate the preparation of the compounds of the formula (I):

EXAMPLE 1

7-anti-(Diphenylmethoxymethyl)-2-(3,4-methylenedioxyphenethyl)-2-azabicyclo[2.2.1]heptane

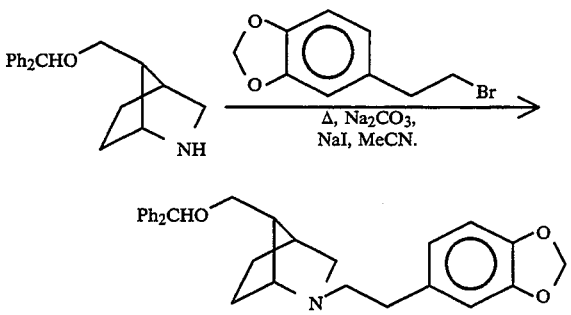

A mixture of 7-anti-diphenylmethoxy-2-azabicyclo[2.2.1]heptane (0.18 g—see Example 10), 3,4-methylenedioxyphenethyl bromide (0.23 g—see Preparation 9), sodium carbonate (0.50 g) and sodium iodide (50 mg) in acetonitrile (20 ml) was heated under reflux for 18 hours and diluted with water and ethyl acetate. The layers were separated and the organic layer was washed with water, dried over magnesium sulphate and evaporated. The residue was purified by chromatography on silica using dichloromethane plus 20% ethyl acetate plus 0–5% methanol as the eluant. Appropriate fractions were combined and evaporated to give the title compound (140 mg, 54%) as a colourless oil which was characterised containing 0.25 equivalents of water.

Analysis %: Found: C,77.9; H,7.1; N,3.2; $C_{29}H_{31}NO_3.0.25\ H_2O$ requires: C,78.1; H,7.1; N,3.1.

EXAMPLES 2–9

The following compounds were prepared by reacting the appropriate diphenylmethoxy-substituted amine with the appropriate alkylating agent as described in Example 1. The compounds were characterised in the forms indicated.

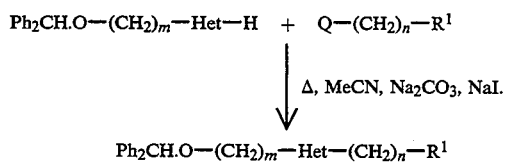

| Example No. | m | Het | n | R¹ | Q | Form Characterised | Analysis % (Theoretical in brackets) C | H | N |
|---|---|---|---|---|---|---|---|---|---|
| 2 | 1 |  | 1 |  | Cl | Oil | Characterised by its $^1$H-NMR spectrum. $^1$H-NMR(CDCl$_3$)δ = 7.18–7.40(10H, m); 7.13(1H, s); 7.01(1H, d, J=8Hz); 6.78(1H, d, J=8Hz); 5.96(2H, s); 5.32(1H, s); 3.83(2H, q, J=8Hz); 3.65(1H, broad s); 3.57(2H, quintet, J=7Hz); 2.90(2H, broad s); 2.10–2.60(3H, m); 1.45–1.70(3H, m). | | |

-continued

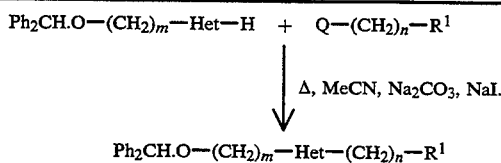

| Example No. | m | Het | n | R¹ | Q | Form Characterised | Analysis % (Theoretical in brackets) C | H | N |
|---|---|---|---|---|---|---|---|---|---|
| 3 | 0 | | 2 | benzodioxole | Br | Oil | 78.5 (78.7 | 6.3 6.8 | 3.3 3.3) |
| 4 | 0 | | 2 | benzodioxole | Br | Oil | 79.4 (79.7 | 7.1 7.1 | 3.4 3.0) |
| 5 | 1 | | 2 | benzodioxole | Br | Oil | Characterised by its ¹H-NMR spectrum. ¹H-NMR(CDCl₃)δ=7.18–7.40(10H, m); 6.57–6.78(3H, m); 5.92(2H, s); 5.29(1H, s); 3.44(1H, broad s); 2.20–3.35(9H, m); 1.05–1.70(5H, m). | | |
| 6 | 0 | | 2 | benzofuran | Br | Oil | 81.8 (82.0 | 7.5 7.6 | 3.3 3.2) |
| 7 | 0 | | 2 | p-tolyl | Br | Oil | 84.2 (84.6 | 8.1 8.1 | 3.4 3.4) |
| 8 | 0 | | 2 | indanyl | Br | Oil | 85.0 (85.1 | 8.1 8.1 | 3.1 3.2) |
| 9 | 0 | | 2 | p-tolyl | Br | Oil | Characterised by its ¹H-NMR spectrum. ¹H-NMR(CDCl₃)δ=7.22–7.50(10H, m); 7.08(4H, s); 5.53(1H, s); 3.64–3.72(1H, m); 2.63–3.12(8H, m); 2.37(3H, s); 1.20–2.08(7H, m). | | |

The preparation of the amine starting materials used in the Examples 2–9 is described in Examples 10–15.

EXAMPLE 10

7-anti-(Diphenylmethoxymethyl)-2-azabicyclo[2.2.1-]heptane

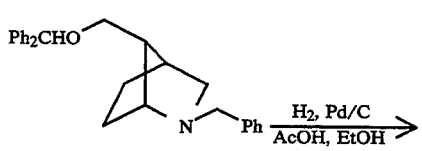

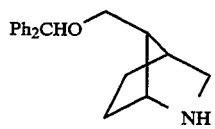

A solution of 2-benzyl-7-anti-(diphenylmethoxymethyl)-2-azabicyclo[2.2.1]heptane (2.30 g—see Example 16) and acetic acid (1.0 ml) in ethanol (200 ml) was stirred at 40°–50° C. under an atmosphere of hydrogen (50 psi=344.7 kPa) in the presence of 5% palladium-on-charcoal (250 mg) for 17 hours, filtered and evaporated to give the desired compound as a colourless oil (1.69 g, 96%) which was characterised as containing 0.75 equivalents of water.

Analysis %: Found: C,78.6; H,7.8; N,4.4; C₂₀H₂₃NO.0.75 H₂O requires: C,78.3; H,8.0; N,4.6.

EXAMPLES 11–15

The following compounds were prepared by catalytically hydrogenating the appropriate N-benzyl amine as described in Example 10. The compounds were characterised in the forms indicated.

$$Ph_2CH-O-(CH_2)_m-Het-CH_2Ph$$
$$\Big\downarrow H_2, Pd/C, EtOH, AcOH$$
$$Ph_2CH.O-(CH_2)_m-Het-H$$

The preparation of the N-benzyl starting materials used in these Examples is described in Examples 22, 23, 24, 17 and 18 respectively.

| Example No. | m | Form Characterised | Analysis % (Theoretical in brackets) | | |
|---|---|---|---|---|---|
| | | | C | H | N |
| 11 | 0 | oil, 0.25 equivalents of water | 80.4 (80.4 | 7.7 7.6 | 4.8 4.9) |
| 12 | 0 | oil, hemi-hydrate | 80.0 (80.0 | 7.8 7.9 | 3.9 4.2) |
| 13 | 1 | oil | Characterised by its ¹H-NMR spectrum ¹H-NMR(CDCl₃)δ= 7.15–7.40(10H, m); 5.29(1H, s); 3.57 (1H, s); 2.04–3.30(6H, m); 0.75–1.60(5H, m). | | |
| 14 | 0 | oil | 81.1 (81.9 | 7.8 7.9 | 4.8 4.8) |
| 15 | 0 | oil | Characterised by its ¹H-NMR spectrum. ¹H-NMR(CDCl₃)δ= 7.18–7.50(10H, m); 5.52(1H, s); 3.64(1H, d, J=8Hz); 2.90–3.30 (4H, m); 1.20–2.30 (7H, m). | | |

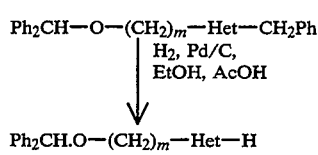

EXAMPLE 16

2-Benzyl-7-anti-(diphenylmethoxymethyl)-2-azabicyclo[2.2.1]heptane

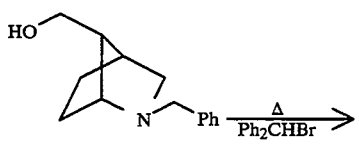

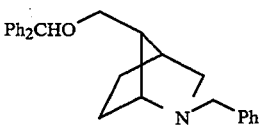

A mixture of 2-benzyl-2-azabicyclo[2.2.1]heptane-7-anti-methanol (4.34 g—commercially available) and bromodiphenylmethane (4.94 g) was heated at 140°–150° C. for 1 hour and dissolved in ethyl acetate (200 ml). The resulting solution was washed with 5% aqueous sodium carbonate solution, dried over magnesium sulphate and evaporated. The residue was chromatographed on silica using dichloromethane plus 0–10% ethyl acetate followed by dichloromethane plus 1–10% methanol as eluant. Appropriate fractions were combined and evaporated to give the desired compound as a colourless oil (4.90 g, 64%) which was characterised as a hemihydrate.

Analysis %: Found: C,83.1; H,7.5; N,3.7; C₂₇H₂₉NO.0.5H₂O requires: C,82.7; H,7.6; N,3.6.

EXAMPLE 17

2-Benzyl-6-exo-diphenylmethoxy-2-azabicyclo[2.2.2]octane

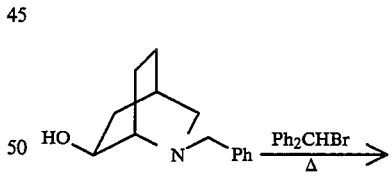

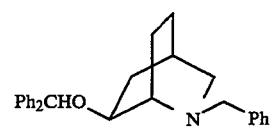

The title compound was prepared as described in Example 16 but using 2-benzyl-2-azabicyclo[2.2.2]octan-6-exo-ol (see U.S. Pat. No. 4,013,668) instead of 2-benzyl-2-azabicyclo[2.2.1]heptane-7-anti-methanol.

The title compound was obtained as a colourless oil (3.39 g, 86%).

Analysis %: Found: C,84.4; H,7.5; N,3.6; C₂₇H₂₉NO requires: C,84.5; H,7.6; N,3.6.

EXAMPLE 18

2-Benzyl-6-endo-diphenylmethoxy-2-azabicyclo[2.2.2]octane

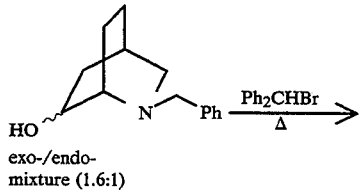

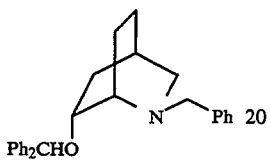

A mixture of 2-benzyl-2-azabicyclo[2.2.2]octan-6-exo-ol and 2-benzyl-2-azabicyclo[2.2.2]octan-6-endo-ol (940 mg; ratio 1.6:1 by $^1$H-NMR—see Preparation 3) and bromodiphenylmethane (1.05 g) was heated at 150° C. for 1.5 hours and dissolved in dichloromethane. The resulting solution was washed with 5% aqueous sodium carbonate solution; dried over sodium sulphate and evaporated. The residue was purified by chromatography on silica using dichloromethane plus 0–4% saturated methanolic ammonia solution as eluant. Appropriate fractions were combined and evaporated to give the desired compound as a colourless oil (250 mg, 16%) which was characterised by its $^1$H-NMR spectrum.

$^1$H-NMR (CDCl$_3$) δ=7.20–7.55 (15H, m); 5.45 (1H, s); 3.60–4.04 (3H, m); 3.12 (1H, d, J=6 Hz); 2.93 (1H, broad s); 2.65 (1H, broad s); 1.18–2.14 (7H, m).

Fractions from the above chromatography which contained the above 6-endo-product contaminated with the corresponding 6-exo-isomer were also combined and evaporated to give a colourless oil (0.82 g) which was shown by $^1$H-NMR to consist of 2-benzyl-6-exo-diphenylmethoxy-2-azabicyclo[2.2.2]octane and 2-benzyl-6-endo-diphenylmethoxy-2-azabicyclo[2.2.2]octane in an approximate ratio of 1:1. A portion of this oil was used in Example 19.

EXAMPLE 19

6-exo-Diphenylmethoxy-2-azabicyclo[2.2.2]octane and 6-endo-diphenylmethoxy-2-azabicyclo[2.2.2]octane (1:1)

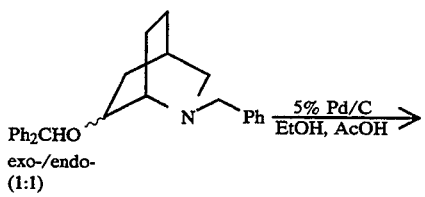

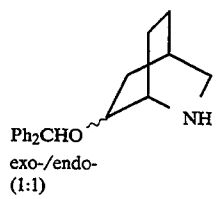

The mixture of title compounds was prepared as described in Example 10 but using 2-benzyl-6-exo-diphenylmethoxy-2-azabicyclo[2.2.2]octane and 2-benzyl-6-endo-diphenylmethoxy-2-azabicyclo[2.2.2]octane (ratio 1:1—see Example 18) instead of 2-benzyl-7-anti-(diphenylmethoxymethyl)-2-azabicyclo[2.2.1]heptane. The mixture of title compounds was obtained as a colourless oil (540 mg, 92%) which was shown by $^1$H-NMR to be a mixture of the 6-exo- and 6-endo-isomers in an approximate ratio of 1:1 and which was used directly in the preparation of Examples 20 and 21.

EXAMPLES 20 and 21

6-exo-Diphenylmethoxy-2-(3,4-methylenedioxyphenethyl)-2-azabicyclo[2.2.2]octane hemihydrate and 6-endo-diphenylmethoxy-2-(3,4-methylenedioxyphenethyl)-2-azabicyclo[2.2.2]octane hydrate

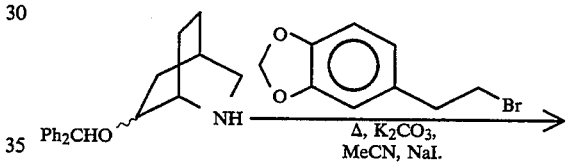

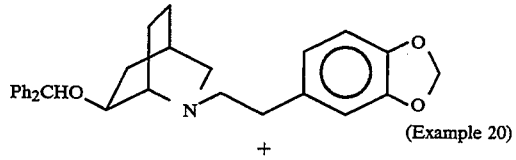

(Example 20)

+

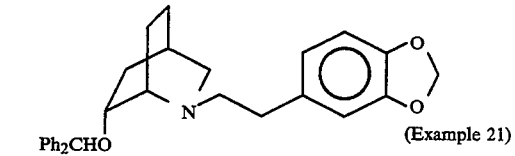

(Example 21)

The title compounds were prepared as described in Example 1 by reacting a mixture of 6-exo-diphenylmethoxy-2-azabicyclo[2.2.2]octane and 6-endo-diphenylmethoxy-2-azabicyclo[2.2.2]octane (ratio=1:1, see Example 19) with 3,4-methylenedioxyphenethyl bromide. Work-up as described in Example 1 followed by separation of the residue by chromatography on silica using hexane: 2-propanol:saturated aqueous ammonia (96:4:1) as eluant afforded the title 6-exo- and 6-endo compounds.

EXAMPLE 20 (exo-isomer)

Analysis %: Found: C,77.2; H,7.4; N,3.0; C$_{29}$H$_{31}$NO$_3$.½H$_2$O: C,77.3; H,7.2; N,3.1.

EXAMPLE 21 (endo-isomer)

Analysis %: Found: C,75.4; H,7.3; N,2.9; Calculated for C$_{29}$H$_{31}$NO$_3$.H$_2$O: C,75.8; H,7.2; N,3.0.

EXAMPLE 22

2-Benzyl-6-exo-diphenylmethoxy-2-azabicyclo[2.2.1-]heptane hydrobromide

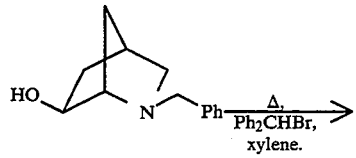

A mixture of 2-benzyl-2-azabicyclo[2.2.1]heptan-6-exo-ol (0.61 g—see Preparation 1 and J. Het. Chem., 395, 9, [1972]) and bromodiphenylmethane (1.48 g) in xylene (10 ml) was heated under reflux for 2 hours, diluted with ethyl acetate, washed with water, dried over sodium sulphate and evaporated. The residue was purified by chromatography on silica using dichloromethane plus 20% ethyl acetate plus 0–5% methanol as the eluant. Appropriate fractions were combined and evaporated to give the desired product as a colourless oil (0.88 g, 65%).

Analysis %: Found: C,71.1; H,6.5; N,3.2; $C_{26}H_{27}NO.HBr$ requires: C,69.3; H,6.2; N,3.1.

EXAMPLE 23

2-Benzyl-6-exo-diphenylmethoxy-2-azaadamantane hydrobromide

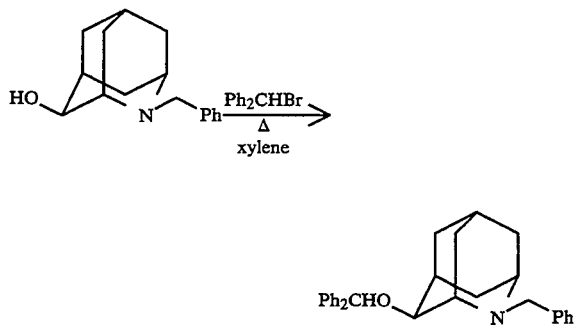

This was prepared as described in Example 22 using 2-benzyl-2-azaadamantan-6-exo-ol (see J. Org. Chem., 3822, 39, [1974] and 3091, 98, [1973]) instead of 2-benzyl-2-azabicyclo[2.2.1]heptan-6-exo-ol. The title compound was obtained as a colourless foam (0.39 g, 27%).

Analysis %: Found: C,70.9; H,6.9; N,2.9; $C_{29}H_{31}NO.HBr$ requires: C,71.0; H,6.5; N,2.9.

EXAMPLE 24

2-Benzyl-6-exo-(diphenylmethoxymethyl)-2-azabicyclo[2.2.1]heptane

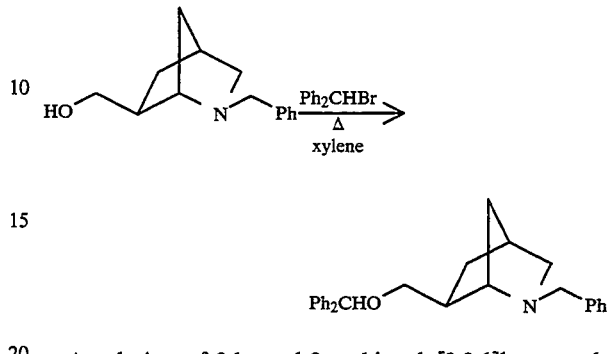

A solution of 2-benzyl-2-azabicyclo[2.2.1]heptane-6-exo-methanol (260 mg—see Preparation 2 but also commercially available) and bromodiphenylmethane (0.49 g) in xylene (20 ml) was heated under reflux for 3 hours, allowed to cool to room temperature, diluted with ethyl acetate, washed with 10% aqueous sodium carbonate solution, dried over sodium sulphate and evaporated. The residue was purified by chromatography on silica using dichloromethane plus 0–20% ethyl acetate followed by dichloromethane plus 20% ethyl acetate plus 2–5% methanol as the eluant. Appropriate fractions were combined and evaporated to give the desired compound as a colourless foam (270 mg, 59%) which was characterised by its $^1$H-NMR spectrum.

$^1$H-NMR (CDCl$_3$) δ=7.09–7.74 (15H, m) ; 5.23 (1H, s) ; 3.98 (2H, broad s); 3.60 (1H, broad s); 3.26 (1H, dd, J=10 and 3 Hz); 3.10 (2H, t, J=10 Hz); 2.77 (1H, broad s); 2.49 (1H, broad s); 1.19–1.95 (5H, m).

EXAMPLE 25

2-α-Diphenylmethoxy-8-(3,4-methylenedioxyphenethyl)-8-azabicyclo[3.2.1]octane

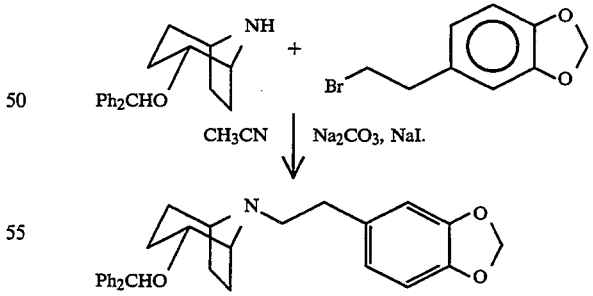

The title compound was prepared as described in Example 1 but using 2-α-diphenylmethoxy-8-azabicyclo[3.2.1]octane (see Example 27) instead of 7-anti-diphenylmethoxy-2-azabicyclo[2.2.1]heptane. The title compound was obtained as a colourless oil (27 mg, 58%) which was characterised as containing 0.25 equivalents of water.

Analysis %: Found: C,78.0; H,7.0; N,3.2; $C_{29}H_{31}NO_3.0.25H_2O$ requires: C,78.1; H,7.1; N,3.1.

EXAMPLE 26

2-β-Diphenylmethoxy-8-(3,4,-methylenedioxyphenethyl)-8-azabicyclo[3.2.1]octane

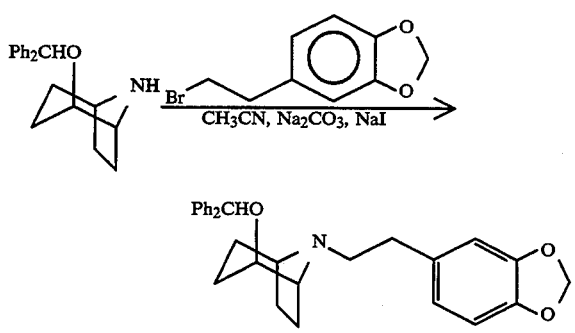

The title compound was prepared as described in Example 1 but using 2-β-diphenylmethoxy-8-azabicyclo[3.2.1]octane (see Example 28) instead of 7-anti-diphenylmethoxy-2-azabicyclo[2.2.1]heptane. The title compound was obtained as a colourless oil (85 mg, 54%) which was characterised as a hemihydrate.

Analysis %: Found: C,77.2; H,6.9; H,3.1; $C_{29}H_{31}NO_3.0.5H_2O$ requires: C,77.1; H,7.2; N,3.1.

EXAMPLE 27

2-α-Diphenylmethoxy-8-azabicyclo[3.2.1]octane

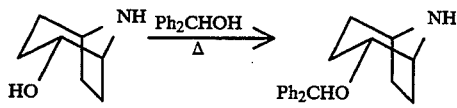

A mixture of 2-α-hydroxy-8-azabicyclo[3.2.1]octane (123 mg—see Preparation 10), para-toluenesulphonic acid monohydrate (237 mg) and benzhydrol (248 mg) in toluene (5 ml) was heated under reflux using a Dean-Stark apparatus for 4 hours. The mixture was partitioned between 2M aqueous sodium hydroxide solution and ether and the organic layer was dried over sodium sulphate and evaporated. The residue was purified by chromatography on silica using dichloromethane plus 0–10% methanol as eluant. Appropriate fractions were combined and evaporated to give the title compound as a colourless oil (51 mg, 17%) which was characterised as a hydrate.

Analysis %: Found: C,76.5; H,7.5; N,4.5; $C_{20}H_{23}NO.H_2O$ requires: C,77.1; H,8.1; N,4.5.

EXAMPLE 28

2-β-Diphenylmethoxy-8-azabicyclo[3.2.1]octane

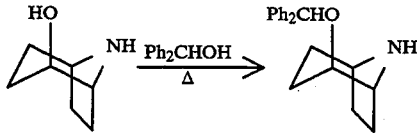

The title compound was prepared as described in Example 27 but using 2-β-hydroxy-8-azabicyclo[3.2.1]octane (see Preparation 11) instead of 2-α-hydroxy-8-azabicyclo[3.2.1]octane. The title compound was obtained as a colourless oil (118 mg, 55%) which was characterised containing 1.33 equivalents of water.

Analysis %: Found: C,75.7; H,7.6; N,4.4; $C_{20}H_{23}NO.1.33H_2O$ requires: C,75.7; H,8.1; N,4.4.

The following Preparations illustrate the preparation of certain starting materials used in the Examples:

Preparation 1

2-Benzyl-2-azabicyclo[2.2.1]heptan-6-exo-ol [see also J. Het. Chem., 1972, 9(2), 395].

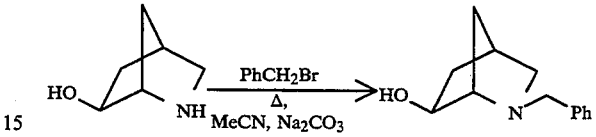

A mixture of 2-azabicyclo[2.2.1]heptan-6-exo-ol (0.75 g—commercially available), benzyl bromide (0.68 g), sodium carbonate (0.50 g) and sodium iodide (50 mg) in acetonitrile (20 ml) was heated under reflux for 16 hours, diluted with ethyl acetate, washed with water, dried over sodium sulphate and evaporated to give the desired compound as a colourless oil, 0.67 g (94%), which was characterised as containing 0.25 equivalents of water.

Analysis %: Found: C,75.4; H,8.3; N,6.7; $C_{13}H_{17}NO.0.25H_2O$ requires: C,75.2; H,8.4; N,6.7.

Preparation 2

2-Benzyl-2-azabicyclo[2.2.1]heptane-6-exo-methanol

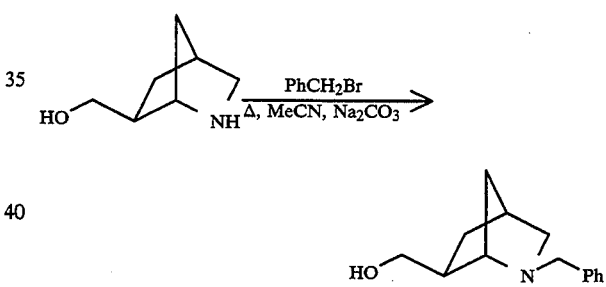

This was prepared as described in Preparation 1 using 2-azabicyclo[2.2.1]heptane-6-exo-methanol (commercially available) instead of 2-azabicyclo[2.2.1]heptan-6-exo-ol. The title compound was obtained as a colourless oil (0.32 g, 55%) which was characterised by its $^1$H-NMR spectrum.

$^1$H-NMR (CDCl$_3$) δ=7.15–7.41 (5H, m) ; 3.63 (2H, AB, J=15 Hz); 3.33–3.48 (2H, m); 3.20 (1H, s); 2.68–2.78 (1H, m); 2.14–2.40 (3H, m); 1.46–1.66 (3H, m); 1.27 (1H, d, J=8 Hz); 1.00–1.17 (1H, m).

Preparation 3

2-Benzyl-2-azabicyclo[2.2.2]octan-6-exo-ol and 2-benzyl-2-azabicyclo[2.2.2]octan-6-endo-ol (ratio 1.6:1)

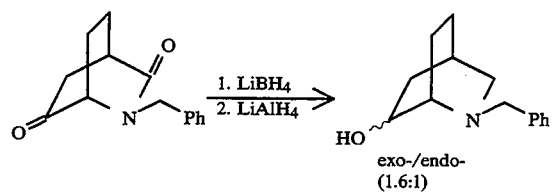

exo-/endo-
(1.6:1)

Lithium borohydride (1.65 g) was added portionwise over 30 minutes to a solution of 2-benzyl-3,6-dioxo-2-azabicyclo[2.2.2]octane (1.70 g—see Preparation 4) in dioxane (125 ml) and the mixture was stirred at room temperature for 17 hours and evaporated. The residue was partitioned between dichloromethane and 5% aqueous sodium carbonate solution and the organic layer was washed with water, dried over sodium sulphate and evaporated. The residue was dissolved in tetrahydrofuran (25 ml) and the solution was added dropwise over 30 minutes to a stirred, ice-cooled suspension of lithium aluminium hydride in tetrahydrofuran (75 ml). The mixture was stirred at room temperature for 72 hours, cooled in ice-water, quenched by the cautious dropwise sequential addition of water (1.14 g) in tetrahydrofuran (10 ml), 15% aqueous sodium hydroxide solution (1.14 g) and water (3.42 g) and filtered. The filtrate was evaporated and the residue was dissolved in dichloromethane, washed with 5% aqueous sodium carbonate solution, dried over sodium sulphate and evaporated. The residue was purified by chromatography on silica using hexane:ethyl acetate:diethylamine (90:10:5) as the eluant. Appropriate fractions were combined and evaporated to give the desired compound as a colourless oil (940 mg, 59%) which was shown by $^1$H-NMR to consist of a mixture of the exo- and endo-isomers in the ratio 1.6:1. This material was used directly in the preparation of Example 18.

Preparation 4

2-Benzyl-3,6-dioxo-2-azabicyclo[2.2.2]octane

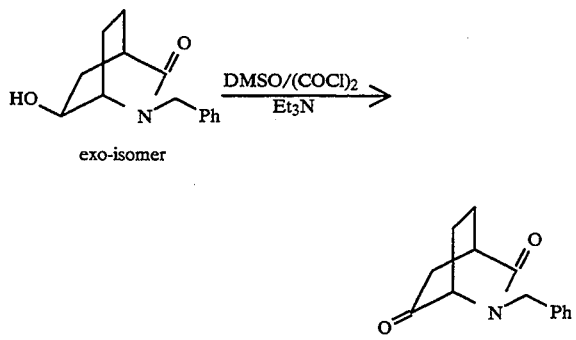

A solution of dimethyl sulphoxide (2.34 g) in dichloromethane (5 ml) was added to a cooled (−60° C.) solution of oxalyl chloride (1.78 g) in dichloromethane (5 ml) and after 2 minutes the mixture was treated with a solution of 2-benzyl-2-azabicyclo[2.2.2]octan-3-one (2.31 g—commercially available) in dichloromethane (10 ml), stirred at −60° C. for 30 minutes, treated with triethylamine (5.05 g), allowed to warm up to room temperature, quenched with water and extracted into dichloromethane. The dichloromethane extracts were dried over sodium sulphate and evaporated. The residue was purified by chromatography on silica using hexane plus 50% ethyl acetate as eluant. Appropriate fractions were combined and evaporated to give the desired compound (2.10 g, 92%) as a colourless oil which was used directly in Preparation 3 without characterisation or further purification.

Preparation 5

5-(2-Hydroxyethyl)-2,3-dihydrobenzofuran

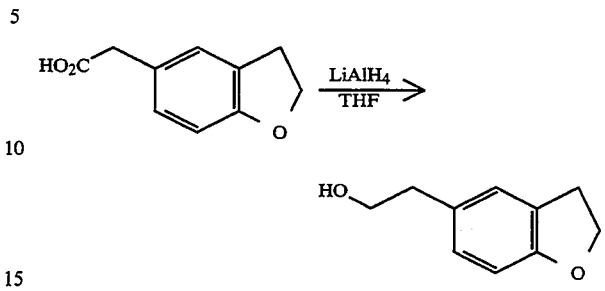

A solution of (2,3-dihydrobenzofuran-5-yl)acetic acid (4.9 g—see EP-A-132130) in anhydrous tetrahydrofuran (50 ml) was added dropwise over 10 minutes to a stirred suspension of lithium aluminium hydride (1.57 g) in anhydrous tetrahydrofuran (50 ml) at 0° C. The mixture was allowed to warm to room temperature and stirred for 1 hour. Water (1.5 ml) was cautiously added dropwise followed by 10% aqueous sodium hydroxide solution (1.5 ml) and water (4.5 ml). The mixture was filtered and the inorganic salts washed with ethyl acetate. The filtrate and washings were combined and evaporated to give the title compound as an oil, yield 3.3 g.

$^1$H-NMR (CDCl$_3$) δ=7.10 (s, 1H); 7.00 (d, 1H); 6.75 (m, 1H); 4.65–4.55 (m, 2H); 3.90–3.75 (m, 2H); 3.30–3.15 (m, 2H); 2.90–2.80 (m, 2H); 1.85–1.75 (brs, 1H) ppm.

Preparation 6

5-(2-Bromoethyl)-2,3-dihydrobenzofuran

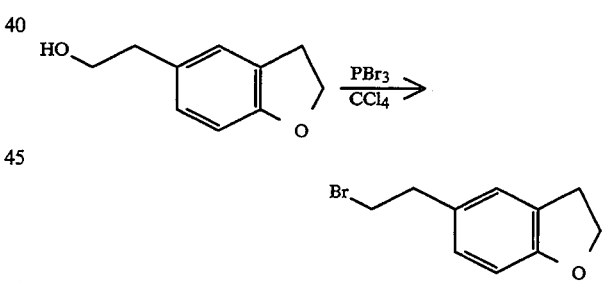

Phosphorus tribromide (0.37 g) was added to a solution of 5-(2-hydroxyethyl)-2,3-dihydrobenzofuran (0.612 g) (see Preparation 5) in carbon tetrachloride (3 ml) and the mixture was heated under reflux for 3 hours. On cooling to room temperature, the mixture was partitioned between 10% aqueous sodium carbonate solution (20 ml) and dichloromethane (20 ml). The layers were separated and the aqueous layer was extracted twice with dichloromethane. The combined dichloromethane extracts were dried over magnesium sulphate and evaporated to give the title compound as an oil which crystallised on standing, yield 0.584 g, m.p. 60°–62° C.

$^1$H-NMR (CDCl$_3$) δ=7.10 (s, 1H); 7.00–6.95 (d, 1H); 6.80–6.70 (d, 1H); 4.65–4.55 (t, 2H); 3.60–3.50 (t, 2H); 3.25–3.15 (t, 2H); 3.15–3.10 (t, 2H) ppm.

Preparation 7

5-(2-Bromoethyl)indane

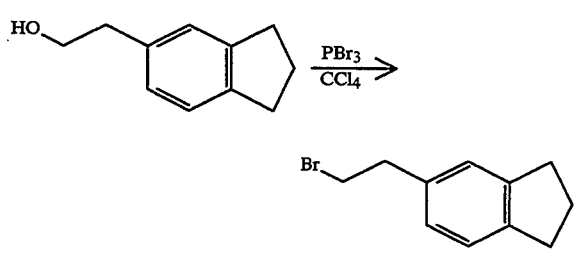

Phosphorus tribromide (3.5 ml) was added dropwise to a solution of 5-(2-hydroxyethyl)indane (14.0 g) (FR-A-2139628) in carbon tetrachloride (100 ml). The mixture was stirred at room temperature for 0.5 hour and then heated under reflux for 2 hours. Ice (100 g) was added and the mixture partitioned between dichloromethane and 10% aqueous sodium carbonate solution. The layers were separated and the aqueous layer extracted twice with dichloromethane. The combined dichloromethane extracts were dried (MgSO$_4$) and evaporated to give an oil which was purified by column chromatography on silica using dichloromethane as the eluant. Appropriate fractions were combined and concentrated in vacuo to give the title compound as a colourless oil, yield 10.5 g.

$^1$H-NMR (CDCl$_3$) δ=7.30–7.00 (m, 3H); 3.60 (m, 2H); 3.20 (m, 2H); 3.00–2.85 (m, 4H); 2.20–2.05 (m, 2H) ppm.

Preparation 8

3,4-Methylenedioxyphenethyl alcohol

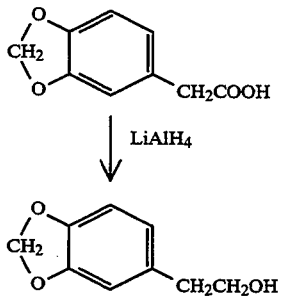

3,4-Methylenedioxyphenylacetic acid (18.0 g) was added portionwise over 30 minutes to a stirred, ice-cooled suspension of lithium aluminium hydride (4.0 g) in ether (400 ml) and the mixture was stirred at room temperature for two hours, quenched by the cautious addition of saturated aqueous ammonium chloride solution and filtered. The filtrate was washed with 10% aqueous sodium carbonate solution, dried over magnesium sulphate and evaporated to give the title compound as a pale yellow oil (15.01 g, 90%) which was characterised by its $^1$H-NMR spectrum.

$^1$H NMR (CDCl$_3$) δ=6.69–6.83 (3H, m); 5.98 (2H, s); 3.82 (2H, dt, J=7 and 6 Hz); 2.81 (2H, t, J=7 Hz) and 1.44 (1H, t, J=6 Hz, exchangeable with D$_2$O).

Preparation 9

3,4-Methylenedioxyphenethyl bromide

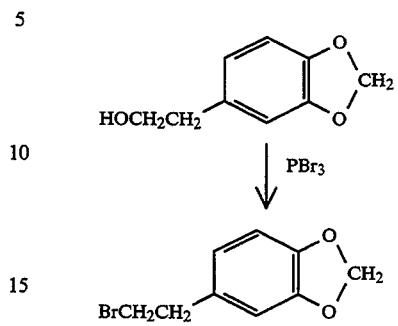

A solution of phosphorus tribromide (8.1 g) in carbon tetrachloride (50 ml) was added dropwise over 30 minutes to a stirred solution of 3,4-methylenedioxyphenethyl alcohol (15.0 g) (see Preparation 8) in carbon tetrachloride (200 ml) and the mixture was heated under reflux for 3 hours, washed sequentially with water (twice), 5M aqueous sodium hydroxide solution and water, dried over magnesium sulphate and evaporated. The residue was purified by chromatography on silica (100 g) using carbon tetrachloride as the eluant. Appropriate fractions were combined and evaporated to give the title compound as a pale yellow oil (8.3 g, 40%) which was characterised by its $^1$H-NMR spectrum.

$^1$H-NMR (CDCl$_3$) δ=6.80 (1H, d, J=8 Hz), 6.75 (1H, s); 6.71 (1H, d, J=8 Hz); 6.00 (2H, s); 3.56 (2H, t, J=7 Hz) and 3.13 (2H, t, J=7 Hz).

Preparation 10

2α-Hydroxy-8-azabicyclo[3.2.1]octane

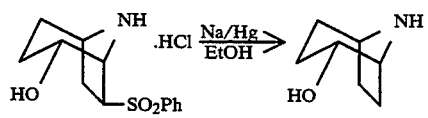

A mixture of 2α-hydroxy-7-syn-phenylsulphonyl-8-azabicyclo[3.2.1]octane hydrochloride (534 mg) (see Preparation 12) and 5% sodium amalgam (10 g) in ethanol (40 ml) was heated under reflux for 16 hours, filtered and evaporated. The residue was purified by chromatography on silica using dichloromethane plus 20% methanol plus 5% concentrated aqueous ammonia solution as eluant. Appropriate fractions were combined and evaporated to give the title compound (106 mg, 42%) as a colourless oil which was characterised containing 0.25 equivalents of water.

Analysis %: Found: C,64.3; H,9.9; N,10.4; C$_7$H$_{13}$NO.0.25H$_2$O requires: C,63.8; H,10.3; N,10.6.

Preparation 11

2β-Hydroxy-8-azabicyclo[3.2.1]octane

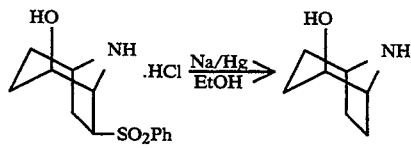

The title compound was prepared as described in Preparation 10 but using 2β-hydroxy-7-syn-phenylsulphonyl-8-azabicyclo[3.2.1]octane hydrochloride (see Preparation 13) instead of 2α-hydroxy-7-syn-phenylsulphonyl-8-azabicyclo[3.2.1]octane hydrochloride. The title compound was obtained as a brown gum (101 mg, 40%) which was characterised by its $^1$H-NMR spectrum.

$^1$H-NMR (CDCl$_3$) δ=3.53 (1H, s), 3.32–3.48 (2H, m); 2.87 (2H, s); 1.22–1.96 (8H, m).

Preparation 12

2α-Hydroxy-7-syn-phenylsulphonyl-8-azabicyclo[3.2.1]octane hydrochloride

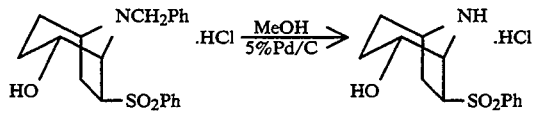

A solution of 8-benzyl-2α-hydroxy-7-syn-phenylsulphonyl-8-azabicyclo[3.2.1]octane hydrochloride (28.4 g) (Tet. Lett. 1990, 27, 3879; see also Chem. Lett. 1989, 593 for a related synthetic procedure) in methanol (284 ml) was stirred at room temperature under an atmosphere of hydrogen (60 psi=413.6 kPa) in the presence of 5% palladium-on-charcoal (2.5 g) for 2 hours, filtered and evaporated. The residue was crystallised from 95% ethanol to give the title compound (19.7 g, 90%) as a colourless solid, m.p. 273° C.

Analysis %: Found: C,57.5; H,6.0; N,4.5; C$_{13}$H$_{17}$NO$_3$S.HCl requires: C,57.4; H,6.0; N,4.6.

Preparation 13

2β-Hydroxy-7-syn-phenylsulphonyl-8-azabicyclo[3.2.1]octane hydrochloride

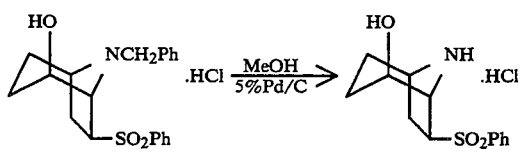

The title compound was prepared as described in Preparation 12 but using 8-benzyl-2β-hydroxy-7-syn-phenylsulphonyl-8-azabicyclo[3.2.1]octane hydrochloride (Tet. Lett. 1990, 27, 3879; see also Chem. Lett. 1989, 593 for a related synthetic procedure) instead of 8-benzyl-2α-hydroxy-7-syn-phenylsulphonyl-8-azabicyclo[3.2.1]octane hydrochloride. The title compound was obtained as a colourless solid (52.9 g, 81%), m.p. 307° C.

Analysis %: Found: C,51.4; H,5.9; N,4.5; C$_{13}$H$_{17}$NO$_3$S.HCl requires: C,51.4; H,6.0; N,4.6.

We claim:

1. A compound of the formula:

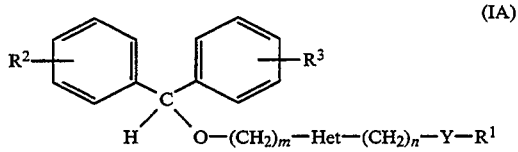

or a pharmaceutically acceptable salt thereof, where
R$^2$ and R$^3$ are each independently H, halo or C$_1$-C$_4$ alkyl;
m is 0, 1 or 2;
n is 1, 2 or 3;
Y is a direct link, O or S; with the proviso that when n is 1, Y is a direct link;
Het is a group of the formula:

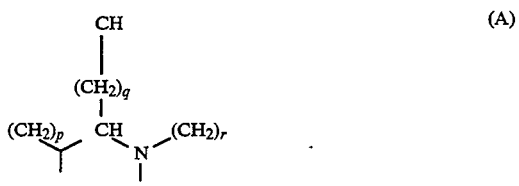

where p is 2, q is 1, and r is 1, the N atom of "Het" being attached to the group (CH$_2$)$_n$ in formula (IA) and other valence attached to the group (CH$_2$)$_m$ in formula (IA) and
R$^1$ is a group of the formula:

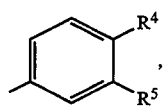

where
R$^4$ and R$^5$ are each independently H, C$_1$-C$_4$ alkyl, C$_1$-C$_4$ alkoxy, —(CH$_2$)$_t$OH, halo, trifluoromethyl, cyano, —(CH$_2$)$_t$NR$^6$R$^7$, —CO(C$_1$-C$_4$ alkyl), —O-CO(C$_1$-C$_4$ alkyl), —CH(OH)(C$_1$-C$_4$ alkyl), —C(OH)(C$_1$-C$_4$ alkyl)$_2$, —SO$_2$NH$_2$, —(CH$_2$)$_t$-CONR$^6$R$^7$ or —(CH$_2$)$_t$COO(C$_1$-C$_4$ alkyl);
R$^6$ and R$^7$ are each independently H or C$_1$-C$_4$ alkyl;
t is 0, 1 or 2.

2. A compound as claimed in claim 1 wherein R$^1$ represents the following group:

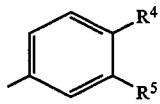

where R$^4$ and R$^5$, are as defined in claim 1.

3. A compound as claimed in claim 1 in which R$^2$ and R$^3$ are both H, m is 0 or 1, n is 1 or 2, and Y is a direct link.

4. A compound as claimed in claim 1, in which said compound is 7-anti-(Diphenylmethoxymethyl)-2-(3,4-methylene-dioxyphenethyl)-2-azabicyclo[2.2.1]heptane.

5. A pharmaceutical composition comprising an effective amount of a compound of the formula (IA) claim 1, or a pharmaceutically acceptable salt thereof, and a pharmaceutically acceptable diluent or carrier.

6. A method of treating irritable bowel syndrome in a patient in need of such treatment, which comprises administering to said patient an effective amount of a compound of the formula (IA) as claim 1, or of a pharmaceutically salt thereof.

* * * * *